United States Patent [19]

Mahood

[11] Patent Number: 5,674,927

[45] Date of Patent: Oct. 7, 1997

[54] AMINE STABILIZED AMORPHOUS PHOSPHITE

[75] Inventor: James A. Mahood, Morgantown, W. Va.

[73] Assignee: General Electric Co., Pittsfield, Mass.

[21] Appl. No.: 559,585

[22] Filed: Nov. 16, 1995

Related U.S. Application Data

[63] Continuation of Ser. No. 325,726, Oct. 19, 1994, Pat. No. 5,468,895.

[51] Int. Cl.$^6$ .................. C08K 5/526; C08K 5/5393; C09K 15/32

[52] U.S. Cl. .................. 524/119; 252/400.24; 524/120; 524/126; 524/153; 524/252; 558/71

[58] Field of Search .................. 524/252, 153, 524/120, 119, 126; 252/400.24; 558/71

[56] References Cited

U.S. PATENT DOCUMENTS

| | | |
|---|---|---|
| 3,376,232 | 4/1968 | Coover et al. . |
| 3,553,298 | 1/1971 | Hodan et al. . |
| 3,560,434 | 2/1971 | Abramoff . |
| 3,644,280 | 2/1972 | Tazewell . |
| 3,654,212 | 4/1972 | Wright . |
| 3,692,730 | 9/1972 | Simo . |
| 3,787,537 | 1/1974 | DeMarcq . |
| 3,886,114 | 5/1975 | Beadle . |
| 3,969,315 | 7/1976 | Beadle . |
| 4,116,926 | 9/1978 | York . |
| 4,318,845 | 3/1982 | Spivack et al. . |
| 4,321,190 | 3/1982 | Costanzi et al. . |
| 4,650,894 | 3/1987 | Fisch et al. . |
| 4,666,959 | 5/1987 | Weissberger et al. . |
| 4,673,701 | 6/1987 | Minagawa et al. . |
| 4,707,509 | 11/1987 | Fisch et al. . |
| 4,824,885 | 4/1989 | Magni et al. . |
| 4,925,888 | 5/1990 | Aumueller et al. . |
| 4,957,956 | 9/1990 | Neri et al. . |
| 5,039,723 | 8/1991 | Haruna et al. . |
| 5,371,263 | 12/1994 | Quotschalla et al. . |
| 5,468,895 | 11/1995 | Mahood . |
| 5,514,742 | 5/1996 | Gardner et al. . |

FOREIGN PATENT DOCUMENTS

| | | |
|---|---|---|
| 49-30327 | 3/1974 | Japan . |

*Primary Examiner*—Veronica P. Hoke

[57] ABSTRACT

A solid amorphous phosphite stabilizer composition is provided which exhibits enhanced hydrolytic stability. The stabilizer composition preferably contains from 10 to 99.9 percent by weight of a phosphorous compound selected from phosphites and phosphonites, and preferably contains from 0.1 to 10 percent by weight of an aliphatic polyamine. The stabilizer composition exhibits enhanced hydrolytic stability, and is preferably in the form of powders or flakes. The stabilizer composition is useful as an additive to polymeric resins as an antioxidant stabilizer.

12 Claims, No Drawings

AMINE STABILIZED AMORPHOUS PHOSPHITE

This is a continuation of application Ser. No. 08/325,726 filed on Oct. 19, 1994 now U.S. Pat. No. 5,468,895.

BACKGROUND OF THE INVENTION

1. Field of the Invention

The present invention relates to solid phosphite stabilizer compositions, and more particularly relates to solid phosphite stabilizer compositions exhibiting enhanced hydrolytic stability.

2. Description of the Related Art

Amine compounds have been utilized in conjunction with phosphites, specifically pentaerythritol phosphites, for enhancing the phosphite's resistance to hydrolysis, see York, U.S. Pat. No. 4,116,926, issued Sep. 26, 1978. The York reference while teaching enhanced stability for the phosphites by utilizing in combination amine compounds and phosphite compounds, can still result in compositions that exhibit water weight gain upon extended exposure to humid conditions at ambient temperature. Accordingly, there is a need to provide pentaerythritol phosphite compositions which exhibit extended resistance to hydrolysis.

SUMMARY OF THE INVENTION

The present invention involves an amorphous (glassy, noncrystalline) solid phosphite stabilizer composition with improved hydrolytic stability, which comprises a melt blend of an organic phosphite and an aliphatic polyamine, more preferably comprises a blend of a crystalline phosphite and an aliphatic primary diamine. The blends have surprisingly and unexpectedly exhibited superior hydrolytic stability compared to melt blend compositions comprising the phosphite and triisopropanolamine and compared to ground admixtures of the phosphite and aliphatic polyamine. The solid stabilizer compositions are useful as additives for stabilizing polymeric compositions against thermal oxidative degradation.

DETAILED DESCRIPTION OF THE INVENTION

Suitable phosphorus ester compounds include phosphites and phosphonites. Suitable phosphites include those elected from the general formula

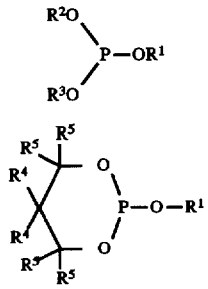

wherein $R^1$, $R^2$, $R^3$ and each $R^4$ represent either equal or different hydrocarbyl radicals, which can be either alkyl, cycloalkyl, aryl, alkaryl or aralkyl radicals; $R^5$ may be the hydrogen, alkyl, cycloalkyl, aryl, alkaryl or aralkyl radicals. The phosphites may also be selected from the general formula:

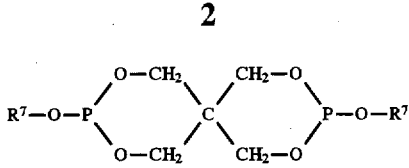

suitable phosphonites include those of the general formula:

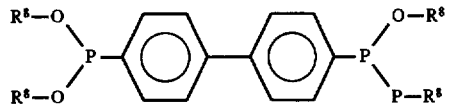

wherein the $R^7$ and $R^8$ radicals independently represent either alkyl, cycloalkyl, aryl, alkaryl or aralkyl radicals.

The phosphite is preferably a pentaerythritol phosphite which may be selected from the group consisting of (a) compounds of the formula

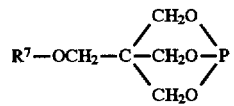

wherein $R^7$ is an aliphatic radical containing 1 to about 20 carbon atoms, a cycloalkyl ring of 5 to about 8 carbon atoms, or an aryl, alkaryl, or aralkyl group of 6 to about 14 carbon atoms, and (b) compounds of the formula

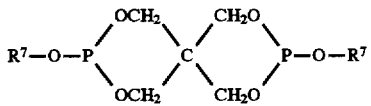

wherein $R^7$ is defined as above. Illustrative of these compounds are those where $R^7$ is an aliphatic radical; $R^7$ can be (a) an alkyl radical such as methyl, ethyl, isopropyl, n-butyl, n-hexyl, 2-ethylhexyl, n-dodecyl, n-tetradecyl, n-octadecyl, and the like, (b) an alkoxyalkyl radical of 2 to about 20 carbon atoms such as methoxyethyl, ethoxyethyl, ethoxypropyl, and the like, and (c) alkoxy carboalkyl radicals of 2 to about 20 carbon atoms such as methoxycarboethyl, propyloxycarboethyl, decyloxycarboethyl, and the like. When $R^7$ is a cycloalkyl ring, illustrations of $R^7$ include cyclopentyl, cyclohexyl, cyclooctyl, and the like. When $R^7$ is an aryl group, phenyl and naphthyl are examples thereof. The aryl group can be halogenated as in a bromophenyl group. Lastly, when $R^7$ is alkaryl of 7 to about 14 carbon atoms; i.e., an alkyl-substituted phenyl or naphthyl group, illustrations thereof are methylphenyl, t-butyl-phenyl, nonylphenyl, and the like; and when $R^7$ is aralkyl of 7 to about 14 carbon atoms; i.e., an aryl-substituted alkyl group, benzyl and phenylethyl are examples thereof. The alkaryl or aralkyl group can be halogenated as in a 2-chloroethylphenyl group. Most preferably the phosphite in its pure (natural) state is a crystalline phosphite.

Examples of the defined pentaerythritol phosphites are dimethylpentaerythritol diphosphite, diethylpentaerythritol diphosphite, didodecylpentaerythritol diphosphite, diocta-decylpentaerythritol diphosphite, diphenylpentaerylthritol diphosphite, ditolylpentaerythritol diphosphite, di-p-chlorophenylpentaerythritol diphosphite, dibenzylpentaerythritol diphosphite, and the like. U.S. Pat. Nos. 2,847,443; 2,961,454; 3,000,850; 3,205,250; and 3,737,485 disclose further examples of the defined compounds.

More preferably, the $R^7$ groups are alkyl radicals of 1 to 20 carbon atoms, cyclohexyl, phenyl, or benzyl. Most preferably, $R^7$ is a higher-alkyl group containing about 6 to about 20 carbon atoms such as n-hexyl, n-octyl, 2-ethylhexyl, n-decyl, n-tetradecyl, n-octadecyl, and the like.

The preferred species is of the formula:

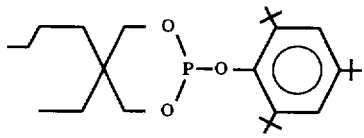

Another preferred phosphite is of the general formula:

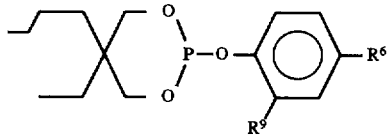

wherein $R^6$ and $R^9$ are each an alkyl group having from 1 to 10 carbon atoms and preferably are each t-butyl group.

The aliphatic polyamine preferably has a boiling point of greater than 175°, more preferably greater than 190°, and most preferably greater than 200° C. The aliphatic polyamine may contain primary, secondary or tertiary amine groups. Preferably the amine groups are primary amine groups. The polyamine may contain 2, 3 or more amine groups, and in other words may be a diamine, triamine or greater polyamine amine. The preferred polyamines are aliphatic primary diamines of the formulas $$H_2N-R^{10}-NH_2$$

wherein $R^{10}$ is selected from $C_6$ to $C_{10}$ divalent alkyl radicals, and more preferably the diamine is selected from 1,6 diaminohexane and 1,10-diaminodecane. Suitable aliphatic secondary diamines may be represented by the general formula:

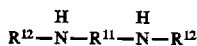

wherein $R^{11}$ is selected from $C_1$ to $C_{10}$ divalent alkyl radicals and $R^{12}$ is selected from $C_1$ to $C_{10}$ monovalent alkylratical. Suitable aliphatic tertiary diamines may be represented by the general formula

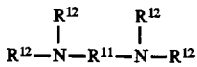

wherein $R^{11}$ and $R^{12}$ are defined as above. Most preferably the polyamine is an aliphatic primary diamine.

The present invention also involves a process involving the melt blending of a crystalline phosphite and a polyamine to form a melt blend, and cooling the melt blend to form an amorphous solid phosphite composition. The process may also involve storing the phosphite for a period in excess of 10 days (possibly in humid conditions (>60% relative humidity)) at ambient temperature, and then compounding the phosphite composition with a thermoplastic polymer such as a polyolefin, for example polypropylene for thermal oxidative stability thereof.

The stabilizer composition of the present invention comprises from 10 percent by weight to 99.9 percent by weight of the phosphite based on the total weight of the stabilizer composition, more preferably from 90 to 99.8 percent by weight thereof, more preferably from 96 to 99.5 percent by weight thereof, and most preferably from 97 to 99 percent by weight thereof. The polyamine is preferably present at a level of from 0.1 to 10 percent by weight based on the total weight of the stabilizer composition, more preferably from 0.2 to 5 percent by weight thereof, more preferably present at a level of from 0.5 to 4 percent by weight thereof, and most preferably present at a level of from 1 to 3 percent by weight thereof. The stabilizer composition is in the form of amorphous (non-crystalline) particles, such as powders and pellets. The stabilizer composition preferably contains less than 10 percent by weight of other materials such as polymeric materials and other organic materials such as waxes, synthetic and petroleum dried lubricating oils and greases; animal oils such as for example fat, tallow, lard, cod liver oil, sperm oil; vegetable oil such as caster, linseed, peanut, cod seed, and the like; fuel oil, diesel oil, gasoline, and the like. In other words, the stabilizer composition, is preferably substantially free of other materials, in other words, containing less than 1 percent of other organic materials, and more preferably is free of other organic materials. Preferably, the stabilizer composition is essentially free of monoamines, such as triisopropylamine. The compositions of the present invention are preferably amorphous to ensure homogeneity of the compositions. The present compositions are preferably obtained by melt mixing rather than simple mechanical blending or solution blending, and surprisingly and unexpectedly the compositions made by melt mixing show superior hydrolyric stability over similar compositions made by simple mechanical (dry) or solution blending.

EXAMPLES

EXA-H are comparative examples. EX1 and 2 illustrate the present invention. Example A is crystalline bis(2,4 di-tert-butylphenyl) pentaerythritol diphosphite (Phos1). Example B is a ground (mechanical dry blend) admixture of 99 wt % Phos1 and 1% wt % trisisopropanol amine (TIPA). Example C is glass (amorphous) melt blend of 99 wt % Phos1 and 1 wt % TIPA. Example D is a ground admixture of 99 wt % Phos1 and 1 wt % 1,10-diaminodecane (DAD). Example 1 is an amorphous melt blend of 99 wt % Phos1 and 1 wt % DAD. Note the superior properties of Ex1 over ExA-D. Example E was a crystalline state and was a phosphite of the formula

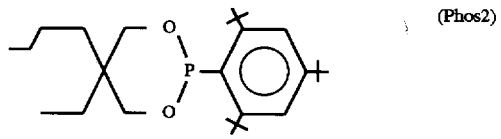

Example F was Phos2 is a glass state. Example G was an amorphous melt blend of 99 wt % Phos2 and 1 wt % Tinuvin 770 Bis(2,2,6,6,-tetra-methylpiperidyl)sebacate. Example H was an amorphous melt blend containing 99 wt % Phos2 and 1 wt % trioctyl amine. Example 2 was an amorphous melt blend containing 99 wt % Phos 2 and 1 wt % 1,10-diaminodecane. Note the superior performance of Example 2 over Example E-H. The samples were exposed to 75% nominal relative humidity at room temperature (approx. 70° F.) for extended periods of time, and these various levels of hydrolytic stability are evidenced by percent weight gain with the lower percentages of weight gain at a given level of exposure time evidencing higher levels of hydrolytic stability.

Example 3 is an amorphous solid (melt blend) of (99 parts by weight (pbw)) bis(2,4 di-t-butylphenyl) pentaerythritol diphosphite and (1 part by weight) 1,6-diamino hexane. Example I is a crystalline form of bis(2,4-di-t-butylphenyl) pentaerythritol diphosphite. Example J is an amorphous solid of bis(2,4 di-t-butylphenyl)pentaerythritol diphosphite. Example K is a blend of bis(2,4 di-t-butylphenyl) pentaerythritol diphosphite (99 pbw) with 1 pbw of octadecylamine. Example L is an amorphous solid (melt blend) of bis(2,4 di-t-butylphenyl) pentaerythritol diphosphite (95.4 pbw) with octadecylamine (4.6 pbw). Example L uses an equal base equivalent level of amine as does Example 3. Examples I–L are comparative examples. Note the substantially enhanced resistance to water weight gain of Example 3 over comparative examples I–L. The substantial enhancement in resistance is both surprising and unexpected.

TABLE 1

Samples Aged at room temperature under nominal 95% relative humidity

| Hours | Ex A | Ex B | Ex C | Ex D | Ex 1 |
|---|---|---|---|---|---|
| 0 | 0.00 | 0.00 | 0.00 | 0.00 | 0.00 |
| 24 | #N/A | 0.74 | 0.12 | 0.45 | 0.01 |
| 48 | #N/A | 1.16 | 0.16 | 0.43 | 0.02 |
| 96 | 0.94 | #N/A | 0.46 | 0.87 | 0.02 |
| 120 | 1.09 | #N/A | 0.61 | 1.14 | 0.09 |
| 168 | #N/A | #N/A | 0.98 | 1.74 | 0.07 |
| 216 | #N/A | #N/A | 1.64 | 2.63 | 0.07 |
| 288 | #N/A | #N/A | 3.10 | 5.49 | 0.09 |
| 336 | #N/A | #N/A | #N/A | #N/A | 0.06 |
| 360 | #N/A | #N/A | #N/A | #N/A | 0.08 |
| 384 | #N/A | #N/A | #N/A | #N/A | 0.13 |
| 456 | #N/A | #N/A | #N/A | #N/A | 0.12 |
| 480 | #N/A | #N/A | #N/A | #N/A | 0.08 |
| 528 | #N/A | #N/A | #N/A | #N/A | 0.03 |
| 552 | #N/A | #N/A | #N/A | #N/A | 0.03 |
| 624 | #N/A | #N/A | #N/A | #N/A | 0.05 |
| 672 | #N/A | #N/A | #N/A | #N/A | 0.06 |
| 720 | #N/A | #N/A | #N/A | #N/A | 0.05 |
| 792 | #N/A | #N/A | #N/A | #N/A | 0.06 |
| 840 | #N/A | #N/A | #N/A | #N/A | 0.06 |
| 888 | #N/A | #N/A | #N/A | #N/A | 0.09 |
| 960 | #N/A | #N/A | #N/A | #N/A | 0.15 |
| 1008 | #N/A | #N/A | #N/A | #N/A | 0.18 |
| 1054 | #N/A | #N/A | #N/A | #N/A | 0.16 |
| 1128 | #N/A | #N/A | #N/A | #N/A | 0.23 |
| 1176 | #N/A | #N/A | #N/A | #N/A | 0.29 |
| 1224 | #N/A | #N/A | #N/A | #N/A | 0.36 |
| 1296 | #N/A | #N/A | #N/A | #N/A | 0.54 |
| 1344 | #N/A | #N/A | #N/A | #N/A | 0.67 |

TABLE 2

Samples Aged at room temperature under nominal 75% relative humidity

| Hours | Ex G | Ex H | Ex 2 | Ex F | Ex E |
|---|---|---|---|---|---|
| 72 | 0.10 | 0.05 | 0.07 | 0.04 | 0.03 |
| 144 | 0.14 | 0.13 | 0.14 | 0.10 | 0.29 |
| 168 | 0.12 | 0.19 | 0.10 | 0.12 | 0.62 |
| 240 | 0.11 | 0.10 | 0.12 | 0.29 | 2.30 |
| 312 | 0.13 | 0.12 | 0.13 | 0.59 | #N/A |
| 456 | 0.13 | 0.09 | 0.12 | 1.82 | #N/A |
| 504 | 0.14 | 0.09 | 0.16 | 2.39 | #N/A |
| 576 | 0.13 | 0.08 | 0.14 | #N/A | #N/A |
| 840 | 0.16 | 0.14 | 0.20 | #N/A | #N/A |
| 936 | 0.18 | 0.20 | 0.13 | #N/A | #N/A |
| 1080 | 0.40 | 0.56 | 0.14 | #N/A | #N/A |
| 1248 | 1.26 | 1.94 | 0.18 | #N/A | #N/A |
| 1416 | #N/A | #N/A | 0.18 | #N/A | #N/A |
| 1584 | #N/A | #N/A | 0.21 | #N/A | #N/A |
| 1776 | #N/A | #N/A | 0.24 | #N/A | #N/A |
| 2112 | #N/A | #N/A | 0.26 | #N/A | #N/A |
| 2280 | #N/A | #N/A | 0.20 | #N/A | #N/A |
| 2496 | #N/A | #N/A | 0.26 | #N/A | #N/A |
| 2952 | #N/A | #N/A | 0.21 | #N/A | #N/A |
| 3312 | #N/A | #N/A | 0.28 | #N/A | #N/A |
| 3528 | #N/A | #N/A | 0.22 | #N/A | #N/A |
| 3936 | #N/A | #N/A | 0.26 | #N/A | #N/A |
| 4608 | #N/A | #N/A | 0.4 | #N/A | #N/A |

TABLE 3

| Hours | Ex I | Ex J | Ex 3 | Ex K | Ex L |
|---|---|---|---|---|---|
| 0 | 0 | 0 | 0 | 0 | 0 |
| 48 | 0.27 | 0.1 | 0.32 | 0.65 | 0.03 |
| 72 | 0.3 | 0.82 | 0.21 | 1.3 | 0.07 |
| 96 | 0.3 | 3.43 | 0.14 | 2.93 | 0.55 |
| 168 | 0.45 | #N/A | 0.09 | #N/A | 1.43 |
| 336 | 1.38 | #N/A | 0.13 | #N/A | #N/A |
| 384 | #N/A | #N/A | 0.13 | #N/A | #N/A |

What is claimed is:

1. A solid amorphous stabilizer composition exhibiting enhanced hydrolytic stability comprising:

(A) a phosphorus ester compound selected from the group consisting of phosphites and phosphonites, said phosphorus ester compound being present at a level of from 90 percent by weight to 99.9 percent by weight based on the total weight of the stabilizer composition, and (B) an aliphatic polyamine having a boiling point greater than 175° C. and containing three or more amine groups, said aliphatic polyamine present at a level of from 0.1 percent by weight to 10 percent by weight based on the total weight of the composition.

2. The stabilizer composition of claim 1 wherein said phosphorous ester compound is present at a level of from 96 to 99.5 percent by weight based on the total weight of the composition.

3. The stabilizer composition of claim 1 wherein said stabilizer composition consists essentially of said phosphorus ester compound and said polyamine.

4. The stabilizer composition of claim 1 wherein said stabilizer composition consists of said phosphorous ester compound and said polyamine.

5. The stabilizer composition of claim 1 wherein said phosphorus ester compound is a phosphite represented by the general formula

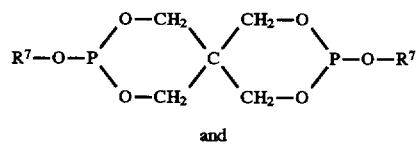

and

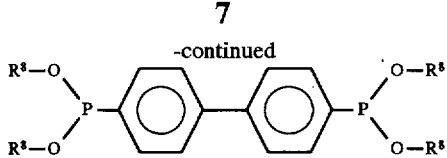

each $R^7$ and $R^8$ radical is independently selected from the group consisting of alkyl, cycloalkyl, aryl, alkaryl or aralkyl radicals.

6. The stabilizer composition of claim 1 wherein said amine groups are primary amine groups.

7. The composition of claim 1 wherein said phosphorous ester compound is 2,4,6-tri-tert-butylphenyl 2-butyl-2-ethyl-1,3-propanediol phosphite.

8. The composition of claim 1 wherein said phosphorus ester compound is bis(2,4-di-tert-butylphenyl) pentaerythritol diphosphite.

9. The composition of claim 1 wherein said composition is in the form of a powder having number average particle size selected from between 10 nanometers and 2 millimeters.

10. The stabilizer composition of claim 1 wherein said composition is in the form of flakes.

11. A method for making a stabilizer composition exhibiting enhanced hydrolytic stability, said method comprising:

(a) melt blending a phosphorus ester compound and an aliphatic polyamine having a boiling point greater than 175° C. and containing three or more amine groups; said composition comprising from 10 to 99.9 weight percent of said phosphorus ester compound and from 0.1 to 10 weight percent of said polyamine based on the total weight of the composition.

12. The method of claim 11 further comprising (b) said composition being exposed to conditions of greater than 50% relative humidity for a period of greater than 1500 hours.

* * * * *